(12) United States Patent
Lee

(10) Patent No.: US 10,342,957 B2
(45) Date of Patent: Jul. 9, 2019

(54) DUAL PASSAGEWAY SAFETY SYRINGE FOR INJECTING A MEDICAMENT INTO NON-VENOUS TISSUE

(71) Applicant: DRGEORGIALEE PTE. LTD., Singapore (SG)

(72) Inventor: Siow Kiang Georgia Lee, Singapore (SG)

(73) Assignee: DRGEORGIALEE PTE. LTD., Singapore (SG)

( * ) Notice: Subject to any disclaimer, the term of this patent is extended or adjusted under 35 U.S.C. 154(b) by 80 days.

(21) Appl. No.: 15/526,967

(22) PCT Filed: Nov. 9, 2015

(86) PCT No.: PCT/SG2015/050440
§ 371 (c)(1),
(2) Date: May 15, 2017

(87) PCT Pub. No.: WO2016/076794
PCT Pub. Date: May 19, 2016

(65) Prior Publication Data
US 2017/0319792 A1 Nov. 9, 2017

(30) Foreign Application Priority Data
Nov. 14, 2014 (SG) .......................... 10201407623V

(51) Int. Cl.
*A61M 25/06* (2006.01)
*A61M 5/32* (2006.01)

(52) U.S. Cl.
CPC ........ *A61M 25/0693* (2013.01); *A61M 5/329* (2013.01); *A61M 5/3286* (2013.01); *A61M 5/3297* (2013.01); *A61M 2005/3201* (2013.01)

(58) Field of Classification Search
CPC ............ A61M 25/0693; A61M 5/3286; A61M 5/3297; A61M 2005/3201
See application file for complete search history.

(56) References Cited

U.S. PATENT DOCUMENTS

| | | | | |
|---|---|---|---|---|
| 4,317,445 A | * | 3/1982 | Robinson | A61M 25/0693 604/168.01 |
| 4,961,729 A | | 10/1990 | Vaillancourt | |
| 5,312,345 A | * | 5/1994 | Cole | A61M 25/0643 604/110 |
| 5,688,246 A | * | 11/1997 | Waitz | A61B 17/3417 604/164.11 |

(Continued)

FOREIGN PATENT DOCUMENTS

| EP | 0139091 A1 | 5/1985 |
|---|---|---|
| EP | 2606828 A1 | 6/2013 |

OTHER PUBLICATIONS

International Search Report in International Application No. PCT/SG2015/050440, filed Nov. 9, 2015.

*Primary Examiner* — Bhisma Mehta
*Assistant Examiner* — James D Ponton
(74) *Attorney, Agent, or Firm* — Saliwanchik, Lloyd & Eisenschenk

(57) ABSTRACT

A device for introducing a medicament 5 into a patient comprises a cannula 8 having an inlet end 12 for the medicament and a discharge end 14 for the medicament and a blood flow passageway 20 that provides a visual indication that the discharge end of the cannula is in a blood vein.

12 Claims, 2 Drawing Sheets

(56) References Cited

U.S. PATENT DOCUMENTS 5,833,668 A * 11/1998 Aguilar ............... A61M 5/3135
                                                               604/227
2013/0245607 A1* 9/2013 Eversull .............. A61M 1/3496
                                                               604/509

* cited by examiner

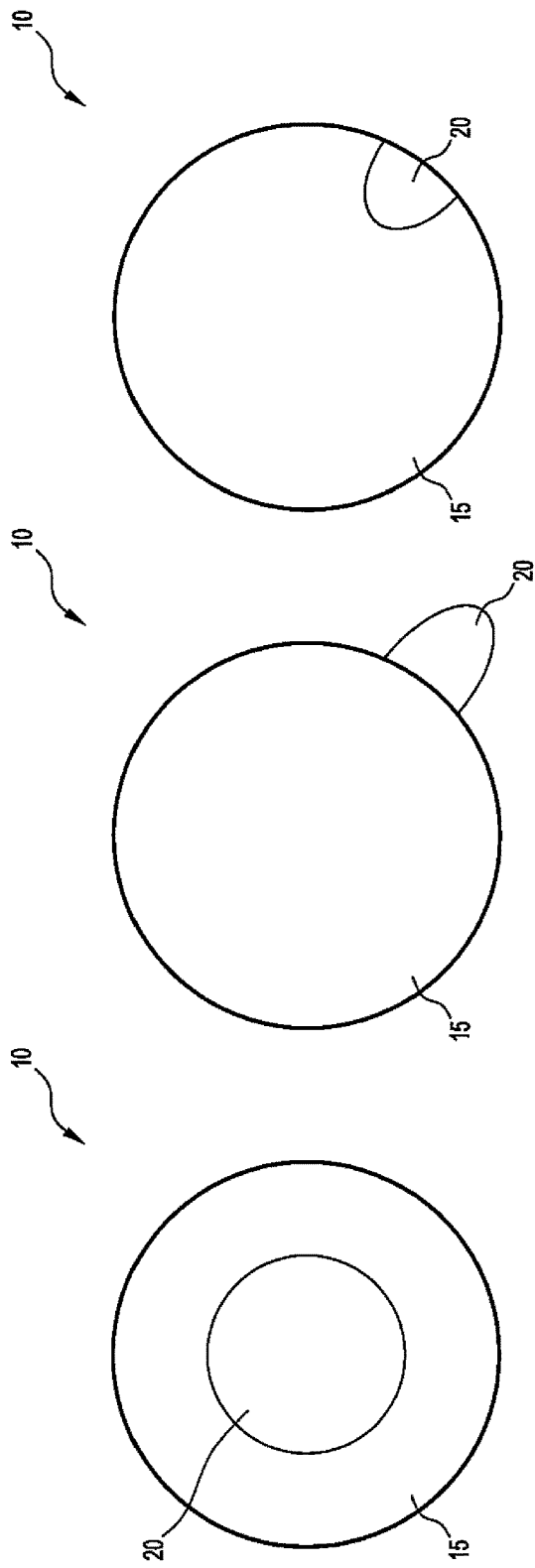

DUAL PASSAGEWAY SAFETY SYRINGE FOR INJECTING A MEDICAMENT INTO NON-VENOUS TISSUE

CROSS-REFERENCE TO RELATED APPLICATIONS

This application is the U.S. national stage application of International Patent Application No. PCT/SG2015/050440, filed Nov. 9, 2015, which claims priority to Singapore Application No. 10201407623V, filed Nov. 14, 2014, the disclosures of each of which are incorporated herein by reference in their entirety.

TECHNICAL FIELD

This invention relates to a medical device for introducing a medicament into or under the skin of a patient.

BACKGROUND

The term "medicament" is understood herein to mean a substance or autologous tissues for use in the medical treatment of a patient, both therapeutic and cosmetic. The term includes by way of example fluids, liquids, pastes, gels or fat tissues or cells that are intended to act as fillers.

The use of medicaments, such as fillers or fat tissue, in or under the skin of a patient is becoming an increasingly common procedure for medical reasons and for cosmetic reasons.

There are known permanent and temporary fillers and other medicaments that are introduced, for example by being injected, in or under the skin of a patient in order to reduce the appearance of lines and wrinkles, plump the face, contour the face or body parts and even fill voids under the skin of the patient. These techniques facilitate augmentation, sculpting and reshaping of the face, cheek, chin, lips, breasts, hands, and other body parts of the patient.

There are a number of options for introducing fillers and other medicaments into the various planes of the skin of a patient or under the skin of the patient described above, including hypodermic needles, catheters, and cannulas (including blunt tip cannulas).

Accidental injection of fillers and other medicaments into blood veins can have serious side effects for patients, including, infection, skin necrosis, skin decomposition, permanent scarring and blindness.

The term "blood vein" is understood herein to include veins, arteries, and blood vessels generally.

As facial sculpting and augmentation becomes increasingly popular, more people are choosing to undergo such procedures. Accordingly, it is desirable to design improved medical devices for introducing fillers and other medicaments into patients.

SUMMARY OF THE INVENTION

In broad terms, the invention provides a device for introducing a medicament into a patient comprising a cannula having an inlet end for the medicament and a discharge end for the medicament and a blood flow passageway that provides a visual indication that the discharge end of the cannula is in a blood vein.

In more particular, although by no means limiting terms, the invention provides a device for introducing a medicament into a patient, the device comprising a cannula having an inlet end for the medicament and a discharge end for the medicament, and a passageway having an opening that is proximal to or level with the discharge end of the cannula, wherein, in use, when the device is accidently positioned in the patient with the discharge end of the cannula and the inlet opening of the passageway penetrating a blood vein there is a flow of blood from the vein through the inlet opening of the passageway and into the passageway that provides a visual indication that the discharge end of the cannula is in the vein.

In use of the device, a medical specialist inserts the device into a patient and selects a target site for the medicament and introduces the medicament via injection through the cannula into the target site. If the medical specialist accidentally positions the device so that the discharge end of the cannula and the inlet opening of the passageway penetrate a blood vein, the pressure of the blood flow in the vein forces blood into the passageway and this provides a visible indication that the device has penetrated the vein. This quickly alerts the medical specialist not to commence introducing the filler or other medicament at the chosen delivery point via the cannula of the device and to withdraw the device and to insert a new device with a new cannula in a new target site. It can be appreciated that the device is an effective means for reducing the accidental introduction of fillers and other medicaments into veins with its possible serious implications.

The discharge end of the cannula may be blunt.

The cannula may be flexible.

The cannula may be a micro cannula.

The cannula may be made from any suitable material. By way of example, the cannula may be made from a medical grade plastic or metal.

The passageway may have an outlet opening that is proximal the inlet end of the cannula.

The cannula may be any suitable transverse cross-section. By way of example, the cannula may be circular in transverse section.

The passageway may be any suitable passageway. By way of example, the passageway may be annular in transverse section.

The cannula and the annular passageway may be coaxial.

The annular passageway may be in the form of an annular tube that fits over the cannula.

An outer wall of the passageway may be transparent.

The device may further comprise a reservoir for storing medicament, with the reservoir being in fluid communication with the inlet end of the cannula.

The device may further comprise an ejector for forcing the medicament from the reservoir along the cannula towards and from the discharge end.

The ejector may be in fluid communication with the inlet opening of the passageway and operable to aid blood flow from the vein should the pressure of the blood be low and not provide a positive backflow when there is accidental puncture of the blood vein. Typically, retracting the ejector creates a negative pressure in the passageway that aids aid blood flow along the passageway.

The ejector may be a plunger.

The device may further comprise a reservoir for collecting blood, with the reservoir being in fluid communication with the inlet end of the passageway.

Various features, aspects, and advantages of the invention will become more apparent from the following description of embodiments of the invention, along with the accompanying drawings in which like numerals represent like components.

BRIEF DESCRIPTION OF THE DRAWINGS

Embodiments of the invention are illustrated by way of example, and not by way of limitation, with reference to the accompanying drawings, of which:

FIG. 2 is a transverse cross-sectional view of the device shown in FIG. 1; and

FIGS. 3 and 4 are transverse cross-sectional views of other embodiments of a medical device according to the invention.

DETAILED DESCRIPTION OF EMBODIMENTS

Figure 1:
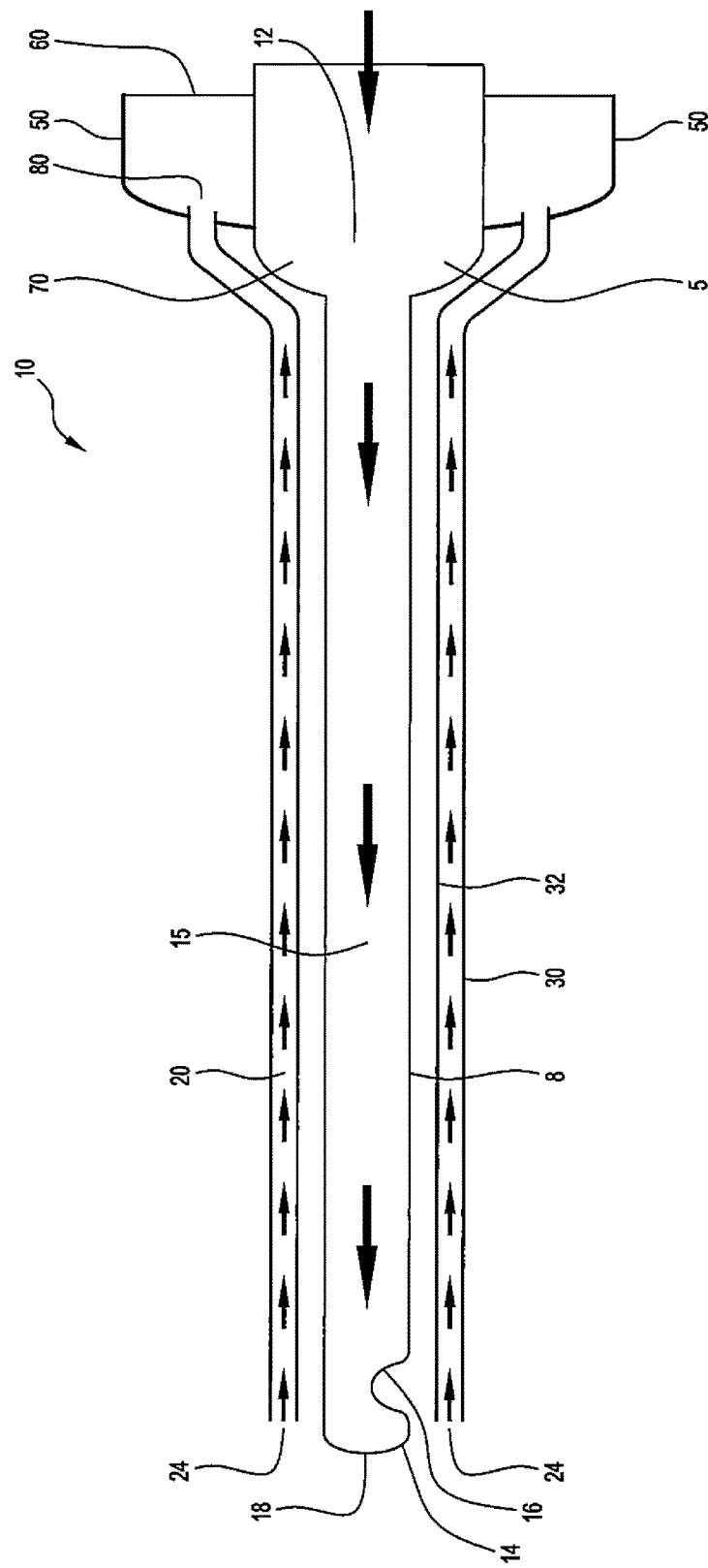
FIG. 1 is a longitudinal cross-sectional view of one embodiment of a medical device according to the invention.

The invention will now be described more fully hereinafter with reference to the accompanying drawings, in which various embodiments, although not the only possible embodiments, of the invention are shown. The invention may be embodied in many different forms and should not be construed as being limited to the embodiments described below.

With reference to FIGS. 1 and 2, one embodiment of the medical device 10 of the invention for introducing a medicament 5 into a patient comprises:
(a) a cannula 8 having a passageway 15 with an inlet end 12 for the medicament 5 and a discharge end 14 for the medicament 5; and
(b) a coaxial annular passageway 20 for providing an indication of blood flow having an annular inlet opening 24 that is proximal to or level with the discharge end 14 of the cannula 8 and an outlet opening 80 that is proximal the inlet end 12 of the cannula 8.

Typically the device 10 is flexible, allowing a medical specialist to manoeuvre the device 10 to a plurality of delivery points in or under the skin of a patient.

In use of the device 10, when a medical specialist accidently positions the device 10 in or under the skin of a patient with the discharge end 14 of the cannula 8 and the inlet opening 24 of the passageway 20 penetrating a blood vein, there is an immediate flow of blood from the vein through the inlet opening 24 of the passageway 20 and into and along the passageway 20 that provides a visual indication that the discharge end 14 of the cannula 8 is in the vein. The blood flow alerts the medical specialist that the cannula is in the wrong position. The medical specialist withdraws the device 10 from the vein (without any medicament having been injected into the vein) and removes the device 10 from the patient and inserts a new device 10 in a new position. If there is no blood flow in the passageway 20 in this new position, the medical specialist can safely inject a required volume of a filler or other suitable medicament into the patient via the cannula. It is evident from the above that the device 10 is an effective means for detecting when a cannula 8 is in a blood vein before any medicament is injected into the vein.

The passageway 20 shown in FIGS. 1 and 2 is in the form of an annular tube defined by an outer wall 30 and a concentric inner wall 32 that fits over the cannula 8. Therefore, the passageway 20 extends along the length of the cannula 8. Typically, the annular tube is formed from a transparent material, such as a transparent medical grade plastic material, so that blood flow can be readily detected.

With further reference to FIG. 1, the device 10 comprises a hub 50 attached to the cannula 8 at the inlet end 12 of the cannula. The hub 50 is only partially shown in FIG. 1. The hub 50 defines a reservoir 70 that holds a measured dose of the medicament 5 to be introduced into the patient. The hub 50 also defines a secondary reservoir 60 that is in fluid communication with the outlet opening 80 of the passageway 20 and is configured to hold blood or other bodily fluids that flow along the passageway 20 into the hub 50. The reservoir 70 and the secondary reservoir 60 are separated to avoid contamination of the medicament 5. The secondary reservoir 60 may be provided with a filter to prevent blood from leaking out of the hub 50 but to allow air to vent through the passageway 20.

The device 10 also comprises an ejector (not shown) for forcing the medicament from the reservoir 70 along the cannula 8 towards and from the discharge end 14 of the cannula 8. The ejector may be a plunger (not shown) that is located in the reservoir 70 for sliding movement from a retracted position to an extended position, with the movement forcing the medicament 5 from the reservoir 70 along the passageway 15 in the cannula 8 and out of the discharge end 14 of the cannula 8. The ejector may be any suitable ejector.

FIG. 1 includes arrows that indicate the direction in which the medicament 5 flows from the inlet end 12 to the discharge end 14 of the cannula 8.

FIG. 1 also includes arrows that indicate the direction of the flow of blood from the inlet opening 24 to the outlet end 80 of the passageway 20 when the cannula 8 and the passageway 20 penetrate a blood vein.

The hub 50 is made from a plastic material, preferably a medical grade plastic material or any other suitable material. The hub 50 can be made from a transparent material. The hub 50 can also include a graduated marking thereon to measure the volume of the medicament 5 as it is being dispensed.

The inlet end 12 of the cannula 8 is disposed within the hub 50 and is in fluid communication with the medicament reservoir 70.

The discharge end 14 of the cannula 8 has a blunt tip 18 and an aperture 16 for discharging the medicament set aback from the tip 18. This minimises mixing of the medicament and blood when the cannula 8 and the passageway 20 penetrate a blood vein. As noted above, mixing of medicament 5 and blood can have serious side-effects for a patient. Furthermore, contact with blood can taint the medicament. If a tainted medicament is injected into the face of a patient, the blood cells within the tainted medicament become deposited within the tissue of the patient and are visible as a bruise on the skin, thereby creating an unsightly discoloration.

The embodiment illustrated in FIGS. 1 and 2 is configured such that the cannula 8 and the passageway 20 are coaxial, with the cannula 8 having a circular transverse cross-section and the passageway 20 having an annular transverse cross-section. The invention is not confined to this embodiment. By way of example, in the alternative, although not the only other, embodiments shown in FIGS. 3 and 4 the passageway 20 is in the form of tubes 20 having generally circular transverse cross-section that are disposed externally of the cannula 8 (FIG. 3) or internally of the cannula 8 (FIG. 4).

Different cannula diameters can be used as required, typically ranging from 20 mm to 80 mm depending on the area of a body to be treated and the viscosity of the filler or concentrate to be injected. The depth of the delivery point under the skin also has a bearing on the size of cannula required. The lower the viscosity of the filler and lesser the depth to be achieved, the smaller the gauge of a cannula is required.

The medicament 5 may be any suitable medicament for a required treatment. Some typically used absorbable fillers include body fat, collagen, hyaluronic acid, calcium hydroxylapatite, CaHA and Poly-L-lactic acid (PLLA). The cannula can also be used to inject gels and highly viscous fluids such as polymethylmethacrylate beads (PMMA microspheres) that are not absorbed by the body but remain in place to fill cavities under the skin. The above fillers can be combined with additional medicaments, such as lidocaine to numb the sensation of the injection when inserting the fillers.

It will be appreciated by persons skilled in the art that numerous variations and modifications may be made to the above-described embodiments, without departing from the scope of the following claims. The present embodiments are, therefore, to be considered in all respects as illustrative and not restrictive.

By way of example, in other embodiments of the invention the ejector may be in communication with the inlet opening 24 of the passageway 20 and operable to aid blood flow from the vein should the pressure of the blood be low and not provide a positive backflow when there is accidental puncture of the blood vein. By way of example, the ejector may be arranged such that retracting the ejector creates a negative pressure in the passageway 20 and aids blood flow along the passageway 20.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, a limited number of the exemplary methods and materials are described herein.

Any discussion of documents, acts, materials, devices, articles or the like which has been included in the present specification is not to be taken as an admission that any or all of these matters form part of the prior art base or were common general knowledge in the field relevant to the present invention as it existed before the priority date of each claim of this application.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The claims defining the invention are as follows:

1. A device for introducing a medicament into a patient, the device comprising:
   a cannula having an inlet end for receiving the medicament and a discharge end with a blunt tip and an aperture set back from the blunt tip for discharging the medicament; and
   a passageway having an inlet opening that is proximal to or level with the blunt tip at the discharge end of the cannula,
   such that, if the device is positioned in the patient with the discharge end of the cannula and the inlet opening of the passageway penetrating a blood vein there is a flow of blood from the vein through the inlet opening of the passageway and into the passageway that provides a visual indication that the discharge end of the cannula is in the vein,
   wherein the passageway is annular in transverse section,
   wherein the cannula and the annular passageway are coaxial, and
   wherein the annular passageway is in the form of an annular tube that fits over the cannula and comprises concentric inner and outer walls between which blood flows from the inlet opening to an outlet opening and the aperture in the cannula is directed at the concentric inner wall, thereby inhibiting blood from entering the aperture.

2. The device defined in claim 1 wherein the cannula is flexible.

3. The device defined in claim 1, wherein the cannula is a micro cannula.

4. The device defined in claim 1 wherein the cannula is made from a medical grade plastic or a metal.

5. The device defined in claim 1, further comprising a hub, in which the passageway has an outlet opening that is proximal to the inlet end of the cannula.

6. The device defined in claim 5 further comprising a reservoir in the hub for storing medicament, with the reservoir being in fluid communication with the inlet end of the cannula.

7. The device defined in claim 6 further comprising an ejector for forcing the medicament from the reservoir along the cannula towards and from the discharge end.

8. The device defined in claim 7 wherein the ejector is a plunger.

9. The device defined in claim 7 wherein the ejector is in fluid communication with the inlet opening of the passageway and is operable to aid blood flow from the vein should the pressure of the blood be low and not provide a positive backflow when there is accidental puncture of the blood vein.

10. The device defined in claim 6 further comprising a secondary reservoir in the hub for collecting blood, with the secondary reservoir being in fluid communication with the inlet end of the passageway.

11. The device defined in claim 1 wherein the cannula is circular in transverse section.

12. The device defined in claim 1 wherein the outer wall of the passageway is transparent.

* * * * *